(12) United States Patent
Beardsley

(10) Patent No.: US 11,446,033 B2
(45) Date of Patent: Sep. 20, 2022

(54) SURGICAL BUTTRESS RELOAD AND TIP ATTACHMENT ASSEMBLIES FOR SURGICAL STAPLING APPARATUS

(71) Applicant: Covidien LP, Mansfield, MA (US)

(72) Inventor: John W. Beardsley, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 17 days.

(21) Appl. No.: 17/088,649

(22) Filed: Nov. 4, 2020

(65) Prior Publication Data

US 2021/0045744 A1 Feb. 18, 2021

Related U.S. Application Data

(63) Continuation of application No. 16/037,367, filed on Jul. 17, 2018, now Pat. No. 10,945,733.
(Continued)

(51) Int. Cl.
*A61B 17/072* (2006.01)
*A61B 17/064* (2006.01)
(Continued)

(52) U.S. Cl.
CPC ...... *A61B 17/07292* (2013.01); *A61B 17/064* (2013.01); *A61B 17/07207* (2013.01); *A61B 2017/00367* (2013.01); *A61B 2017/00477* (2013.01); *A61B 2017/07228* (2013.01); *A61B 2017/07257* (2013.01); *A61B 2017/07271* (2013.01); *A61B 2017/320044* (2013.01); *A61B 2090/038* (2016.02)

(58) Field of Classification Search
USPC ...................................................... 227/176.1
See application file for complete search history.

(56) References Cited

U.S. PATENT DOCUMENTS 3,054,406 A 9/1962 Usher
3,124,136 A 3/1964 Usher
(Continued)

FOREIGN PATENT DOCUMENTS

CA 2282761 A1 9/1998
DE 1602563 U 3/1950
(Continued)

OTHER PUBLICATIONS

Extended European Search Report corresponding to EP 14 16 9739.1, completed Aug. 19, 2014 and dated Aug. 29, 2014; (7 pp).
(Continued)

*Primary Examiner* — Anna K Kinsaul
*Assistant Examiner* — Chinyere J Rushing-Tucker
(74) *Attorney, Agent, or Firm* — Carter, DeLuca & Farrell LLP

(57) ABSTRACT

A surgical stapling apparatus includes a handle assembly, an elongate tubular body, a loading unit including an anvil assembly and a staple cartridge assembly, and a reload assembly. The reload assembly includes a staple cartridge releasably disposed within the staple cartridge assembly of the loading unit, a cartridge buttress releasably secured to the staple cartridge, and an anvil buttress including a proximal portion releasably secured to the staple cartridge and a distal portion releasably coupled to the anvil assembly of the loading unit.

20 Claims, 10 Drawing Sheets

Related U.S. Application Data

(60) Provisional application No. 62/549,226, filed on Aug. 23, 2017.

(51) Int. Cl.
   *A61B 17/00* (2006.01)
   *A61B 17/32* (2006.01)
   *A61B 90/00* (2016.01)

(56) References Cited

U.S. PATENT DOCUMENTS

| | | |
|---|---|---|
| 3,364,200 A | 1/1968 | Ashton et al. |
| 3,499,591 A | 3/1970 | Green |
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Raybum et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Raybum et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |

(56) References Cited

U.S. PATENT DOCUMENTS

| | | |
|---|---|---|
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |

(56) References Cited

U.S. PATENT DOCUMENTS

| | | |
|---|---|---|
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommerberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommerberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommerberger) Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek (nee Prommerberger) et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,931,116 B2 | 4/2018 | Racenet et al. |
| 10,022,125 B2 | 7/2018 | (Prommerberger) Stopek et al. |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |

(56) References Cited

U.S. PATENT DOCUMENTS

| | | |
|---|---|---|
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0012704 A1* | 1/2010 | Tarinelli Racenet ........................ A61B 17/07207 227/180.1 |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0080336 A1 | 4/2012 | Shelton, IV et al. |
| 2012/0145767 A1 | 6/2012 | Shah et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0241499 A1 | 9/2012 | Baxter, III et al. |
| 2012/0253298 A1 | 10/2012 | Henderson et al. |
| 2012/0273552 A1 | 11/2012 | Olson et al. |
| 2013/0146643 A1* | 6/2013 | Schmid .............. A61B 17/0644 227/180.1 |
| 2013/0153636 A1 | 6/2013 | Shelton, IV et al. |
| 2013/0153641 A1 | 6/2013 | Shelton, IV et al. |
| 2013/0256376 A1 | 10/2013 | Barton et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0224686 A1 | 8/2014 | Aronhalt et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157320 A1 | 6/2015 | Zergiebel et al. |
| 2015/0157321 A1 | 6/2015 | Zergiebel et al. |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1* | 5/2016 | Baxter, III ......... A61B 17/0686 227/178.1 |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0278765 A1 | 9/2016 | Shelton, IV et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0055981 A1 | 3/2017 | Vendely et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson, Ph.D et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0235626 A1 | 8/2018 | Shelton, IV et al. |
| 2019/0290267 A1 | 9/2019 | Baxter, III et al. |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2491867 A1 | 8/2012 |
| EP | 2764833 A2 | 8/2014 |
| EP | 2783642 A1 | 10/2014 |
| EP | 3017772 A2 | 5/2016 |
| EP | 3135215 A1 | 3/2017 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 95/16221 A1 | 6/1995 |
| WO | 98/38923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |

OTHER PUBLICATIONS

Extended European Search Report corresponding to EP 14 15 7997.9, completed Sep. 9, 2014 and dated Sep. 17, 2014; (8 pp).

Extended European Search Report corresponding to EP 14 16 8904.2, completed Sep. 10, 2014 and dated Sep. 18, 2014; (8 pp).

Extended European Search Report corresponding to EP 13 19 4995.0, completed Jun. 5, 2014 and dated Oct. 13, 2014; (10 pp).

Extended European Search Report corresponding to EP 13 15 4571.7, completed Oct. 10, 2014 and dated Oct. 20, 2014; (8 pp).

Extended European Search Report corresponding to EP 14 18 1125.7, completed Oct. 16, 2014 and dated Oct. 24, 2014; (7 pp).

Extended European Search Report corresponding to EP 14 18 1127.3, completed Oct. 16, 2014 and dated Nov. 10, 2014; (8 pp).

Extended European Search Report corresponding to EP 14 19 0419.3, completed Mar. 24, 2015 and dated Mar. 30, 2015; (6 pp).

European Office Action corresponding to EP 12 198 776.2 dated Apr. 7, 2015.

European Office Action corresponding to EP 13 156 297.7 dated Apr. 10, 2015.

Australian Examination Report No. 1 corresponding to AU 2011250822 dated May 18, 2015.

European Office Action corresponding to EP 12 186 175.1 dated Jun. 1, 2015.

Chinese Office Action corresponding to CN 201010517292.8 dated Jun. 2, 2015.

Extended European Search Report corresponding to EP 14 17 4814.5 dated Jun. 9, 2015.

Australian Examination Report No. 1 corresponding to AU 2014200584 dated Jun. 15, 2015.

European Office Action corresponding to EP 13 180 881.8 dated Jun. 19, 2015.

(56) References Cited

OTHER PUBLICATIONS

European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
Australian Examination Report No. 1 corresponding to AU 2014200793 dated Sep. 2, 2017.
Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to counterpart Patent Application EP 18190154.7 dated Feb. 4, 2019.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008 (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).

(56) References Cited

OTHER PUBLICATIONS

European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 182911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
European Office Action corresponding to EP 14 17 2681.0 dated May 13, 2016.
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.

(56) References Cited

OTHER PUBLICATIONS

Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
European Office Action dated Sep. 14, 2021 corresponding to counterpart Patent Application EP 18 190 154.7.

* cited by examiner

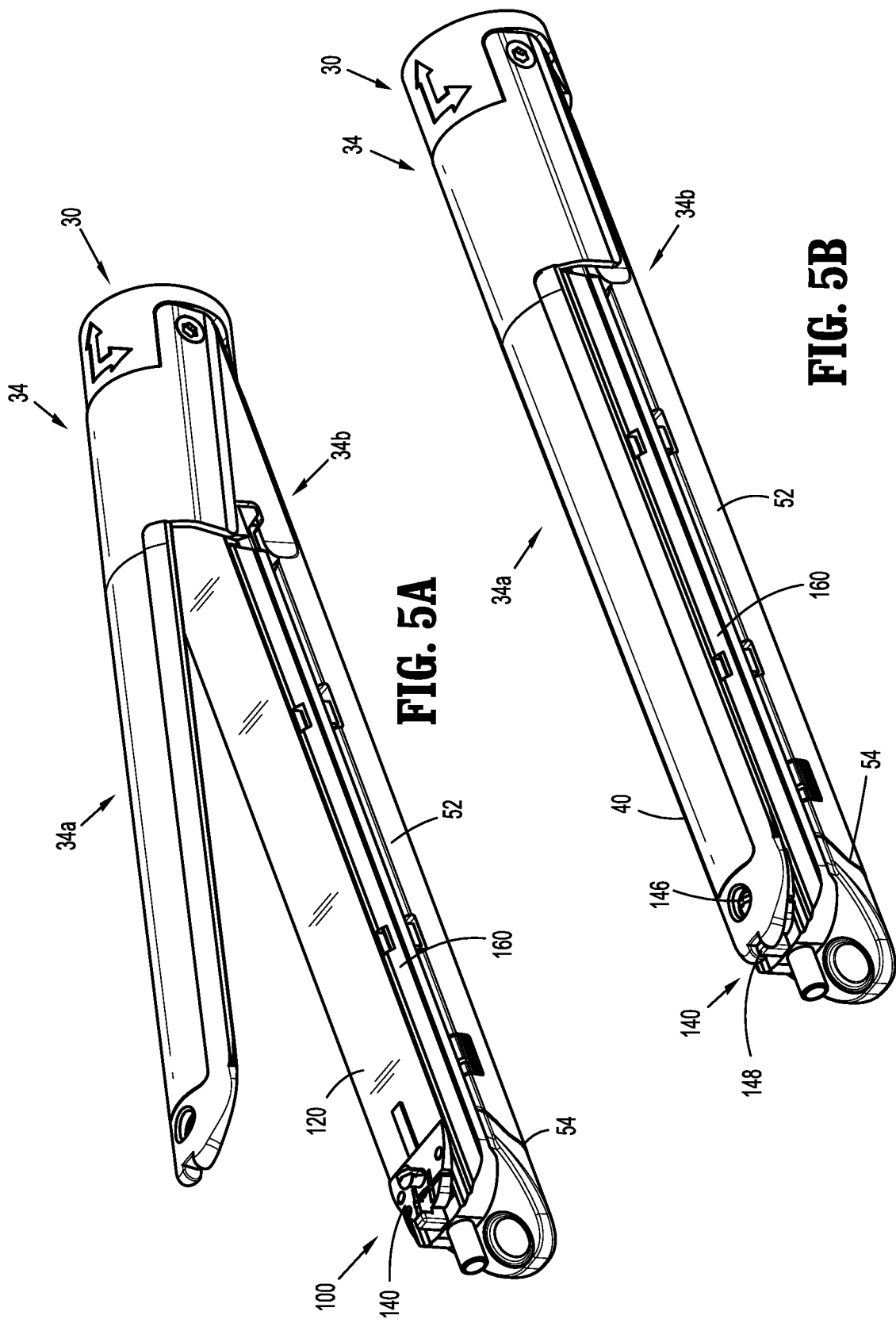

SURGICAL BUTTRESS RELOAD AND TIP ATTACHMENT ASSEMBLIES FOR SURGICAL STAPLING APPARATUS

CROSS-REFERENCE TO RELATED APPLICATIONS

This application is a continuation of U.S. patent application Ser. No. 16/037,367, filed Jul. 17, 2018, which claims the benefit of and priority to U.S. Provisional Patent Application Ser. No. 62/549,226, filed Aug. 23, 2017, the entire disclosure of each of which is incorporated by reference herein.

BACKGROUND

Technical Field

The present disclosure relates to surgical stapling apparatus, and more particularly, to reinforced reload attachment assemblies for releasably securing surgical buttresses to surgical stapling apparatus and/or modifying the tip configuration of the surgical stapling apparatus.

Background of Related Art

Surgical stapling apparatus are employed by surgeons to sequentially or simultaneously apply one or more rows of fasteners, e.g., staples or two-part fasteners, to body tissue for the purpose of joining segments of the body tissue together. Such apparatus generally include a pair of jaws or finger-like structures between which the body tissue to be joined is placed. When the surgical stapling apparatus is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in one of the jaws of the apparatus to cut the body tissue between the lines of staples.

Linear surgical stapling devices are commonly used during surgical procedures to simultaneously seal and cut target tissue, e.g., vasculature, organs, etc. It is not uncommon during such procedures that other tissue, e.g., vasculature or other adherent, connective, or joined tissue, must first be separated from the target tissue before the procedure can continue. Typically, a separate surgical device is used to dissect or separate the other tissue from the target tissue before the target tissue and/or the other tissue is operated upon.

Surgical supports, e.g., meshes or buttress materials, may be used in combination with surgical stapling apparatus to bridge, repair, and/or reinforce tissue defects within a patient such as those occurring, for example, in the abdominal wall, chest wall, diaphragm, or musculo-aponeurotic areas of the body. The surgical support reinforces the staple line as well as covers the juncture of the tissues to reduce leakage prior to healing.

Accordingly, it would be desirable to provide a surgical stapling apparatus that can be used to not only staple and cut tissue but also to separate and dissect tissue and/or to reinforce and seal the staple line.

SUMMARY

According to an aspect of the present disclosure, a surgical stapling apparatus includes a handle assembly, an elongate tubular body, a loading unit including an anvil assembly and a staple cartridge assembly, and a reload assembly. The reload assembly includes a staple cartridge releasably disposed within the staple cartridge assembly of the loading unit, a cartridge buttress releasably secured to the staple cartridge, and an anvil buttress including a proximal portion releasably secured to the staple cartridge and a distal portion releasably coupled to the anvil assembly of the loading unit.

The proximal portion of the anvil buttress may be releasably secured to a trailing portion of the staple cartridge. The trailing portion of the staple cartridge may be disposed proximally of a tissue facing surface of the staple cartridge. Proximal and distal portions of the cartridge buttress may be releasably secured to the tissue facing surface of the staple cartridge.

The reload assembly may further include an anvil adapter releasably engaged with a distal portion of the anvil assembly. In embodiments, the distal portion of the anvil buttress is releasably secured to the anvil adapter. In some embodiments, the reload assembly further includes a retention member releasably securing the distal portion of the anvil buttress to the anvil adapter, and an anvil knife configured to cut the retention member and release the anvil buttress from the anvil adapter.

The anvil adapter may include a button extending therefrom, the button releasably engaged with an opening extending through the distal portion of the anvil assembly. The anvil adapter may include a protrusion disposed at a distal end thereof, the protrusion releasably engaged with a notch defined in a distal end of the anvil assembly. The anvil adapter may include a tip portion having a curved dissecting tip.

The reload assembly may further include a shipping wedge releasably positioned between the cartridge and anvil buttresses.

According to another aspect of the present disclosure, a reload assembly for a loading unit of a surgical stapling apparatus includes a staple cartridge, a cartridge buttress releasably secured to the staple cartridge, and an anvil buttress including a proximal portion releasably secured to the staple cartridge.

The proximal portion of the anvil buttress may be releasably secured to a trailing portion of the staple cartridge. The trailing portion of the staple cartridge may be disposed proximally of a tissue facing surface of the staple cartridge. Proximal and distal portions of the cartridge buttress may be releasably secured to the tissue facing surface of the staple cartridge.

In embodiments, the reload assembly further includes an anvil adapter releasably attached to a distal portion of the anvil buttress. In some embodiments, the reload assembly further includes a retention member releasably securing the distal portion of the anvil buttress to the anvil adapter, and an anvil knife configured to cut the retention member and release the anvil buttress from the anvil adapter.

The anvil adapter may include a button extending therefrom, the button releasably engageable with an opening defined in an anvil assembly of a loading unit. The anvil adapter may include a protrusion disposed at a distal end thereof, the protrusion releasably engageable with a notch defined in an anvil assembly of a loading unit. The anvil adapter may include a tip portion having a curved dissecting tip.

The reload assembly may further include a shipping wedge releasably positioned between the cartridge and anvil buttresses.

Other aspects, features, and advantages will be apparent from the description, drawings, and the claims.

BRIEF DESCRIPTION OF THE DRAWINGS

Various aspects of the present disclosure are described herein below with reference to the drawings, which are incorporated in and constitute a part of this specification, wherein:

FIG. 5A is a side, perspective view of the reload assembly of FIG. 3A positioned within a second jaw member of a tool assembly;

FIG. 5B is a side, perspective view of the reload assembly of FIG. 5A loaded onto a first jaw member of the tool assembly;

DETAILED DESCRIPTION OF THE EMBODIMENTS

Figure 1:
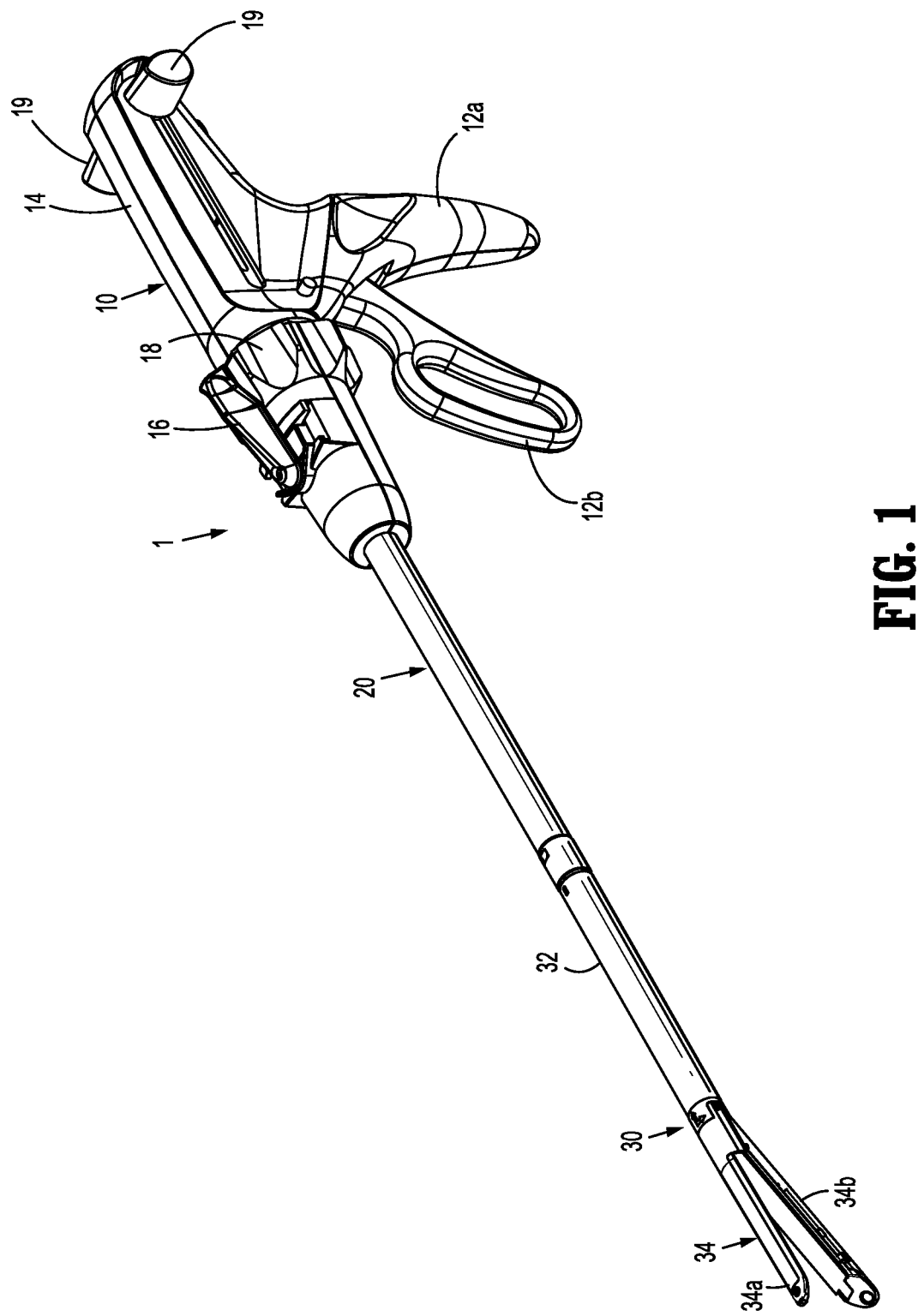
FIG. 1 is a side, perspective view of a surgical stapling apparatus in accordance with an embodiment of the present disclosure.

Embodiments of the present disclosure are now described in detail with reference to the drawing figures wherein like reference numerals identify identical or similar elements in each of the several views. Throughout this description, the term "proximal" refers to a portion of a structure, or component thereof, that is closer to a user, and the term "distal" refers to a portion of the structure, or component thereof, that is farther from the user. Directional reference terms, such as "top," "bottom," "side," and the like, are intended to ease description of the embodiments and are not intended to have any limiting effect on the ultimate orientations of a structure or any parts thereof.

Referring now to FIG. 1, an exemplary surgical stapling apparatus or surgical stapler 1 is shown for use in stapling tissue in accordance with an embodiment of the present disclosure. The surgical stapling apparatus 1 generally includes a handle assembly 10, an elongate tubular body 20 extending distally from the handle assembly 10, and a loading unit 30 extending distally from the elongate tubular body 20. The loading unit 30 includes a housing portion 32 and a tool or jaw assembly 34 including first and second jaw members 34a, 34b. The first jaw member 34a and/or the second jaw members 34b is pivotable with respect to the housing portion 32 such that the tool assembly 34 is movable between an open position in which the first and second jaw members 34a, 34b are spaced apart with respect to each other, and a closed position in which the first and second jaw members 34a, 34b are substantially adjacent each other.

The handle assembly 10 includes a stationary handle member 12a, a movable handle member 12b, and a barrel portion 14. Actuation of the movable handle member 12b applies lines of staples 60 (FIG. 2) to tissue captured between the first and second jaw members 34a, 34b of the tool assembly 34. An articulation lever 16 is mounted on the forward end of the barrel portion 14 to facilitate articulation of the tool assembly 34. A rotatable member 18 is also mounted on the forward end of the barrel portion 14, adjacent the articulation lever 16. Rotation of the rotatable member 18 relative to the barrel portion 14 rotates the elongate tubular body 20 and the loading unit 30 relative to the handle assembly 10 so as to properly orient the tool assembly 34 relative to tissue to be stapled. A pair of knobs 19 is movably positionable along the barrel portion 14. The pair of knobs 19 is advanced distally to approximate or close the first and second jaw members 34a, 34b of the tool assembly 34 relative to each other, and retracted proximally to unapproximate or open the first and second jaw members 34a, 34b of the tool assembly 34 with respect to each other.

The loading unit 30 is a disposable loading unit ("DLU") that is releasably secured to the elongated tubular body 20 and thus, replaceable with a new loading unit 30. The loading unit 30 may be a single use loading unit ("SULU") that is used one time and then replaced to facilitate multiples uses of the surgical stapling apparatus 1 on a patient. For example, during a surgical procedure, the surgical stapling apparatus 1 can be used to staple and cut tissue, and the entire SULU is replaced after each staple and cut operation of the surgical stapling apparatus 1. The loading unit 30 may be a multi-use loading unit ("MULU") that is re-useable a predetermined number of times. For example, during a surgical procedure, the surgical stapling apparatus 1 can be used to staple and cut tissue, and a reload assembly 100 (see e.g., FIG. 3A) of the MULU is replaced after each staple and cut operation of the surgical stapling apparatus 1 a predetermined number of times before the entire MULU needs to be replaced. Alternatively, the loading unit 30 may be permanently affixed to the elongated tubular body 20.

Figure 2:
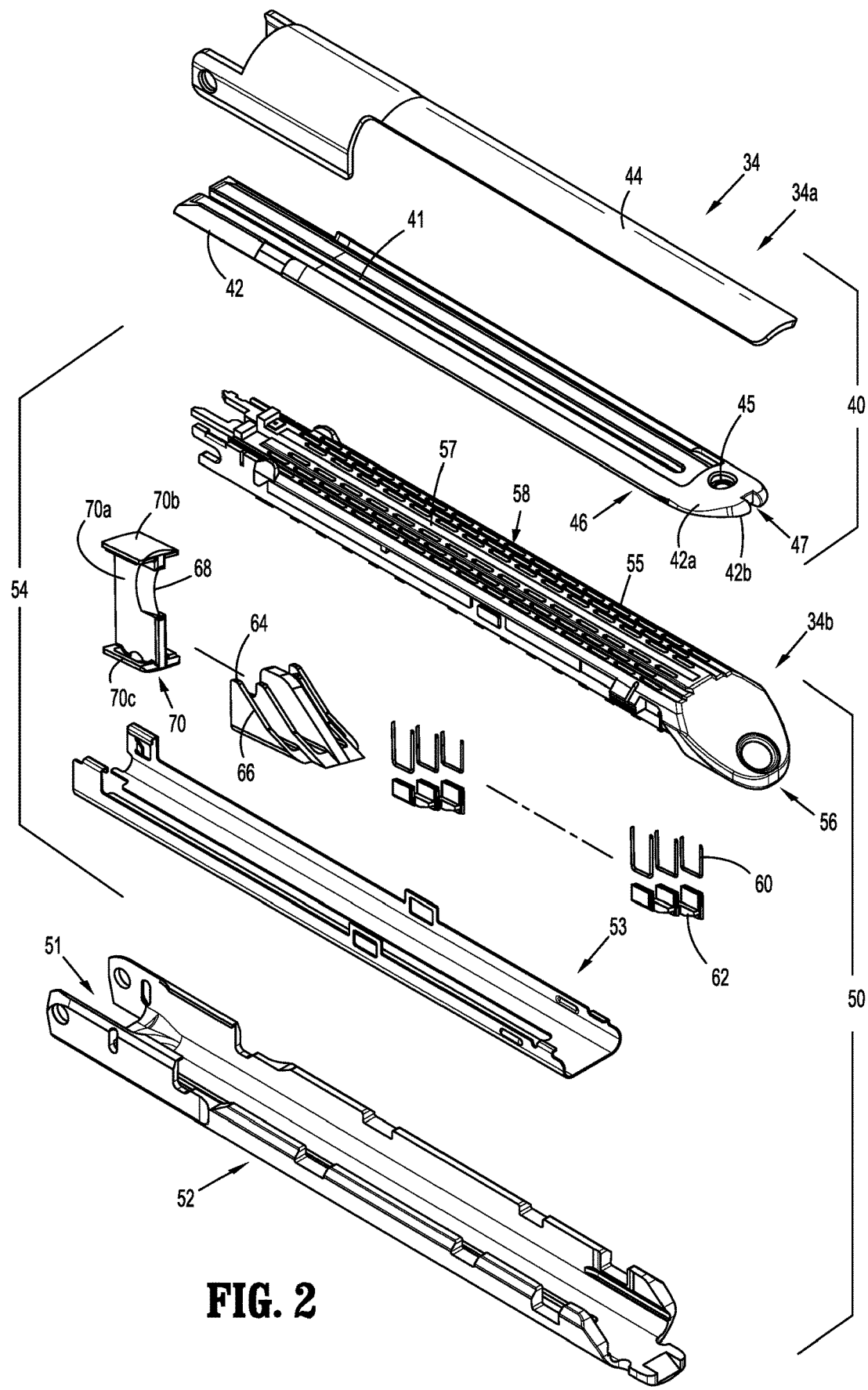
FIG. 2 is an exploded, perspective view of a tool assembly of the surgical stapling apparatus of FIG. 1 in accordance with an embodiment of the present disclosure.

As seen in FIG. 2, the first jaw member 34a of the tool assembly 34 includes an anvil assembly 40 and the second jaw member 34b of the tool assembly 34 includes a staple cartridge assembly 50. The anvil assembly 40 includes an anvil plate 42 and a cover plate 44 secured over the anvil plate 42. The anvil plate 42 has a central longitudinal slot 41 formed therein and a plurality of staple forming pockets/cavities 43 (FIG. 6C) defined in an inward or tissue facing surface thereof 46. A distal portion 42a of the anvil plate 42 includes an opening 45 defined therethrough, and a notch 47 defined in a distal end 42b thereof.

The staple cartridge assembly 50 includes a cartridge carrier 52 defining an elongated support channel 51 configured and dimensioned to selectively receive and support a staple cartridge 54 therein. The staple cartridge 54 may be removably and/or replaceably attached to the cartridge carrier 52 by, for example, a snap-fit connection, a detent, a latch, among other types of connectors within the purview of those skilled in the art. The staple cartridge 54 includes a support plate 53 and a cartridge body 56 having an inward or tissue facing surface 58 defining staple pockets or retention slots 55 formed therein for receiving a plurality of fasteners or staples 60 and staple pushers 62. A central longitudinal slot 57 is formed in and extends along a substantial length of the cartridge body 56 to facilitate passage of a knife blade 68 therethrough.

The knife blade 68 is defined in a distal edge of a central wall portion 70a of an I-beam 70 that is operatively associated with the tool assembly 34. The central wall portion 70a of the I-beam 70 is slidably disposed between the anvil and staple cartridge assemblies 40, 50, with upper and lower rails 70b, 70c of the I-beam 70, respectively, supported in the anvil and staple cartridge assemblies 40, 50. The I-beam 70 is coupled to an elongated drive beam 72 (FIG. 6C) which is configured to engage a drive member (not shown) of the elongated tubular body 20 (FIG. 1) of the surgical stapling apparatus 1 when the loading unit 30 is engaged therewith. The drive member imparts axial movement to the elongated drive beam 72 and thus, the I-beam 70, from the handle assembly 10. Accordingly, during operation of the surgical stapling apparatus 1, distal advancement of the I-beam 70 causes an actuation sled 64 to translate through the staple cartridge 54 and to advance cam wedges 66 of the actuation sled 64 into sequential contact with the staple pushers 62 which, in turn, cause the staple pushers 62 to translate vertically within the staple pockets 55 and urge the staples 60 from the staple pockets 55 towards the tissue facing surface 46 of the anvil plate 42 of the anvil assembly 40.

For a detailed description of the structure and function of exemplary surgical stapling apparatus, reference may be made to U.S. Pat. Nos. 6,241,139, 6,330,965, and 7,819,896, the entire contents of each of which are incorporated herein by reference. It should be appreciated that principles of the present disclosure are equally applicable to surgical stapling apparatus having other configurations such as, for example, the types described in U.S. Pat. Nos. 5,964,394, 7,128,253, and 7,334,717, the entire contents of each of which are incorporated herein by reference. Accordingly, it should be understood that a variety of surgical stapling apparatus may be utilized with the reinforced reloads and/or tip attachment assemblies of the present disclosure. For example, laparoscopic or open staplers, such as, for example, GIA™, Endo GIA™, TA™, and Endo TA™ staplers and/or linear and radial reloads with, for example, Tri-Staple™ technology, available through Medtronic (North Haven, Conn.) may be utilized with the surgical buttress reloads and/or tip attachment assemblies of the present disclosure.

Figure 3A:
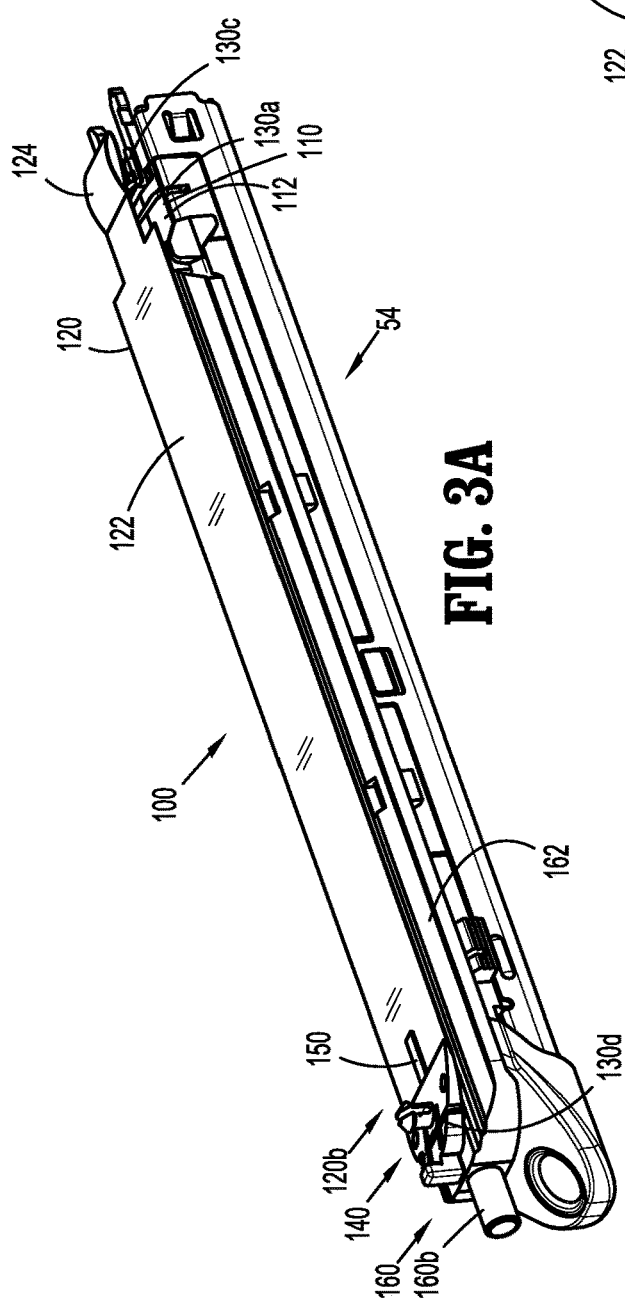
FIG. 3A is a side, perspective view of a reload assembly for use with a loading unit of the surgical stapling apparatus of FIG. 1 in accordance with an embodiment of the present disclosure.
Figure 3B:
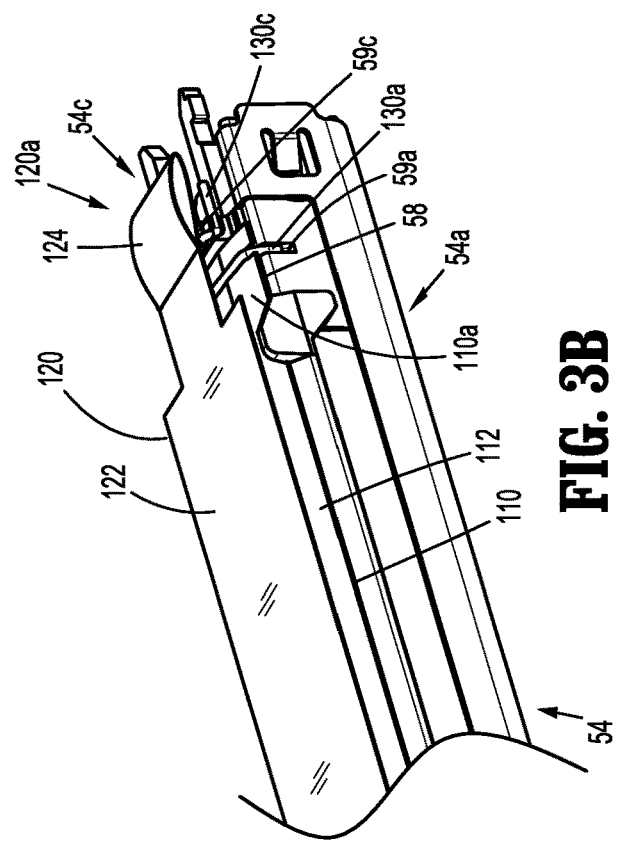
FIG. 3B is a side, perspective view of a proximal portion of the reload assembly of FIG. 3A, with a shipping wedge of the reload assembly removed.
Figure 3C:
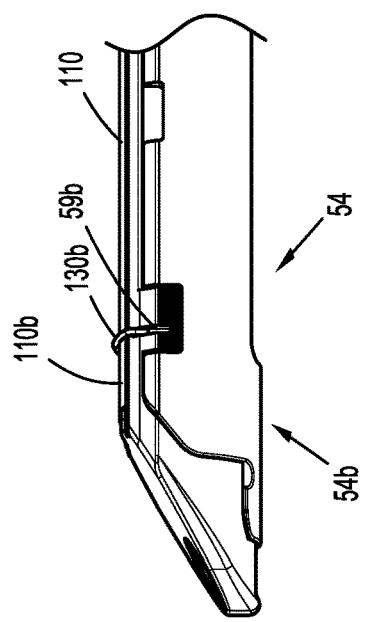
FIG. 3C is a side, plan view of a distal portion of a staple cartridge and a cartridge buttress of the reload assembly of FIG. 3A.

With reference now to FIGS. 3A-3C, a reload assembly 100 for use with the loading unit 30 (FIG. 1) is shown. The reload assembly 100 may be pre-loaded (e.g., by the manufacturer) onto the loading unit 30, and/or additional or replacement reload assemblies 100 may be secured to the loading unit 30, as needed or desired. The reload assembly 100 includes a staple cartridge 54, as well as surgical buttresses 110, 120, a plurality of retention members 130a-130d, an anvil adapter 140, an anvil knife 150, and a shipping wedge 160.

The surgical buttresses 110, 120 (also referred to herein as cartridge and anvil buttresses 110, 120) are fabricated from biocompatible materials which are bioabsorbable or non-absorbable, natural or synthetic materials. It should be understood that any combination of natural, synthetic, bioabsorbable, and/or non-bioabsorbable materials may be used to form the surgical buttresses 110, 120. The surgical buttresses 110, 120 may be formed from the same material or different materials.

The surgical buttresses 110, 120 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The surgical buttresses 110, 120 described herein may be a single porous or non-porous layer, or include a plurality of layers including any combination of porous and non-porous layers. For example, a surgical buttress may include multiple porous and non-porous layers that are stacked in an alternating manner. In another example, a surgical buttress may be formed in a "sandwich-like" manner wherein the outer layers of the surgical buttress are porous and the inner layer(s) are non-porous, or vice versa. The surgical buttresses 110, 120 may have the same or a different structure of layer(s).

Porous layer(s) in a surgical buttress may enhance the ability of the surgical buttress to absorb fluid, reduce bleeding, and seal a wound. Also, the porous layer(s) may allow for tissue ingrowth to fix the surgical buttress in place. Non-porous layer(s) in a surgical buttress may enhance the ability of the surgical buttress to resist tears and perforations during the manufacturing, shipping, handling, and stapling processes. Also, non-porous layer(s) may retard or prevent tissue ingrowth from surrounding tissues thereby acting as an adhesion barrier and preventing the formation of unwanted scar tissue.

The plurality of retention members 130a-d (also referred to herein as first, second, third, and fourth retention members 130a-130d) are fabricated from biocompatible materials which are any combination of natural, synthetic, bioabsorbable, and/or non-bioabsorbable materials. Each of the retention members 130a-130d is a single continuous elongated structure, and may be in the form of a suture, thread, filament, tether, strap, band, line, wire, cable, etc.

With continued reference to FIGS. 3A-3C, the cartridge buttress 110 includes a body portion 112 configured and dimensioned to overlie the tissue facing surface 58 of the staple cartridge 54, and to be releasably secured thereto via the first and second retention members 130a, 130b. The staple cartridge 54 includes a first pair of recesses 59a formed in opposed side edges of a proximal portion 54a of the staple cartridge 54, and a second pair of recesses 59b formed in opposed side edges of a distal portion 54b of the staple cartridge 54. The first and second pairs of recesses 59a, 59b may have a circular or non-circular configuration dimensioned to retain portions of the respective first and second retention members 130a, 130b therein (e.g., frictionally engaging, pinching, or otherwise constricting the first and second retention members 130a, 130b) to maintain placement of the first and second retention members 130a, 130b across respective proximal and distal portions 110a, 110b of the cartridge buttress 110. Alternatively, the first and second retention members 130a, 130b may be secured to the staple cartridge 54 via other attachment features or methods, such as chemical attachment features (e.g., adhesives), mechanical attachment features (e.g., mounting structures such as tabs or pins), and/or attachment methods (e.g., welding), to releasably secure the cartridge buttress 110 to the staple cartridge 54.

The anvil buttress 120 includes a body portion 122 configured and dimensioned to overlie the tissue facing surface 46 (FIG. 6C) of the anvil assembly 40, and a tail portion 124 extending proximally from the body portion 122. While the tail portion 124 is shown as a loop of buttress material, other configurations are envisioned. The tail portion 124 of the anvil buttress 120 is releasably secured to the staple cartridge 54 via the third retention member 130c, and a distal end portion of the body portion 122 of the anvil buttress 120 is releasably secured to the anvil adapter 140 via the fourth retention member 130d (when the staple cartridge 54 is loaded into the cartridge carrier 52 of the staple cartridge assembly 50). It is further envisioned that tail portion 124 of the anvil buttress 120 may be connected to or integral with the cartridge buttress 110.

The staple cartridge 54 includes a third pair of recesses 59c formed in opposed side edges of a trailing portion 54c of the staple cartridge 54, which is disposed proximally of the tissue facing surface 58 of the staple cartridge 54. The tail portion 124 of the anvil buttress 120 is configured and dimensioned to overlie the trailing portion 54c of the staple cartridge 54 and is releasably attached thereto via the third retention member 130c which is retained within the third pair of recesses 59c and extends across the tail portion 124 of the anvil buttress 120 and a path of the knife blade 68 (FIG. 2). As the tail portion 124 of the anvil buttress 120 is releasably secured to the trailing portion 56c of the staple cartridge 54, the tool assembly 34 (FIG. 1) may open, close, and otherwise function (e.g., grasp and/or staple tissue) without putting stress on the third retention member 130c. Thus, the attachment configuration, of the proximal portion 120a of the anvil buttress 120 to the staple cartridge 54, does not interfere with the function of the tool assembly 34 when the anvil buttress 120 is loaded onto the anvil assembly 40.

Figure 4A:
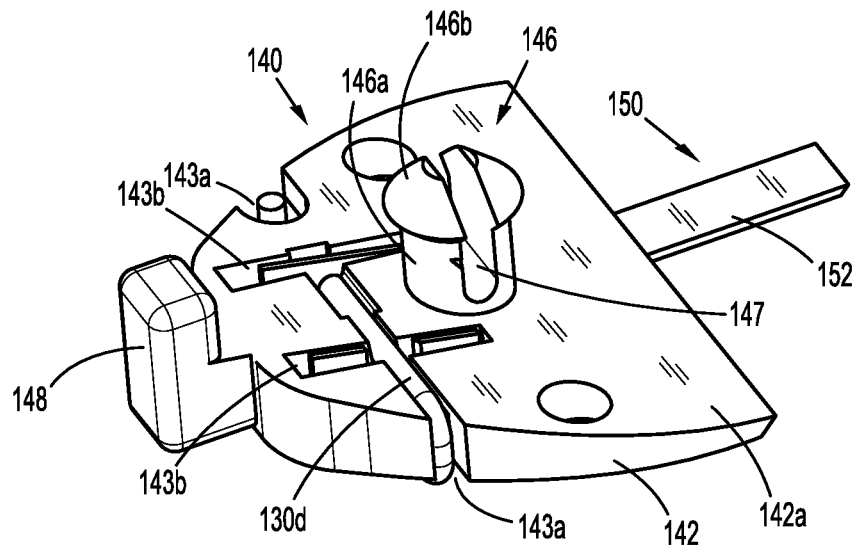
FIG. 4A is a top, perspective view of an anvil adapter, an anvil knife, and a retention member of the reload assembly of FIG. 3A.
Figure 4B:
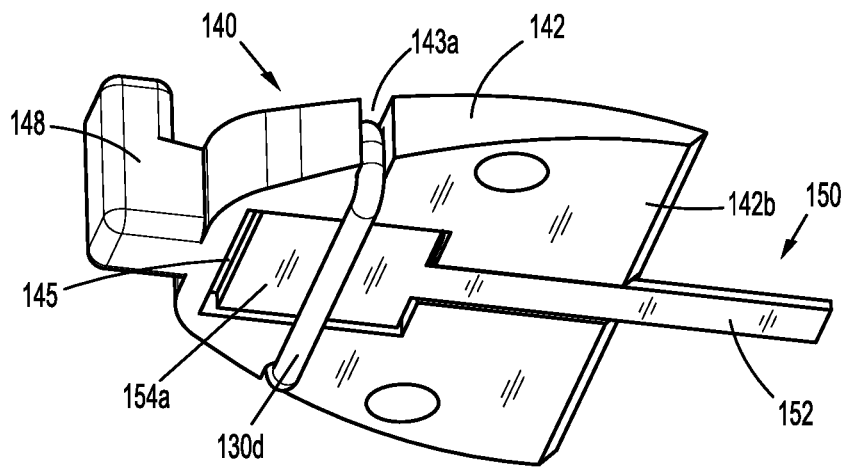
FIG. 4B is a bottom, perspective view of the anvil adapter, the anvil knife, and the retention member of the reload assembly of FIG. 4A.

A distal portion 120b of the anvil buttress 120 is releasably secured to the anvil adapter 140 via the fourth retention member 130d. As shown in FIGS. 4A and 4B, the anvil adapter 140 includes a body portion 142 sized and shaped to correspond with a proximal portion 40a (FIG. 6C) of the anvil assembly 40 such that an anvil facing surface 142a of the body portion 142 abuts the proximal portion 40a of the anvil assembly 40 and a tissue facing surface 142b of the anvil adapter 40 acts as an extension of the tissue facing surface 46 (FIG. 6C) of the anvil assembly 40. The anvil adapter 140 includes a pair of recesses 143a formed in opposed side edges of the body portion 142, and a pair of elongated openings 143b defined through the body portion 142 between the pair of recesses 143a.

Figure 4C:
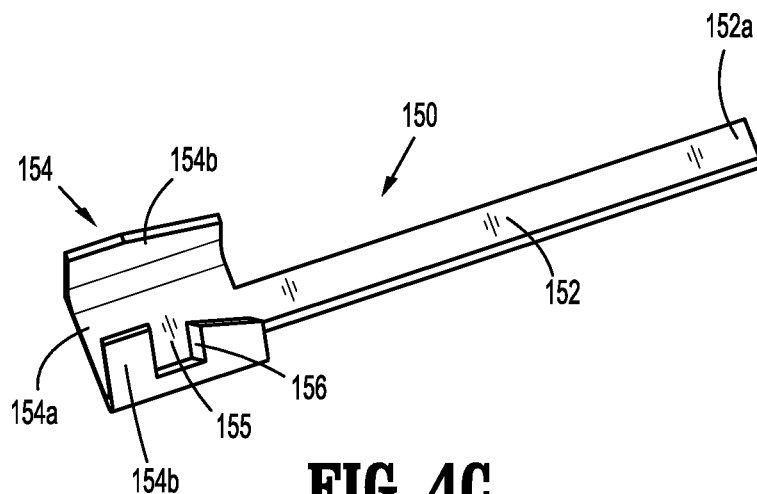
FIG. 4C is a top, perspective view of the anvil knife of FIGS. 4A and 4B.
Figure 4D:
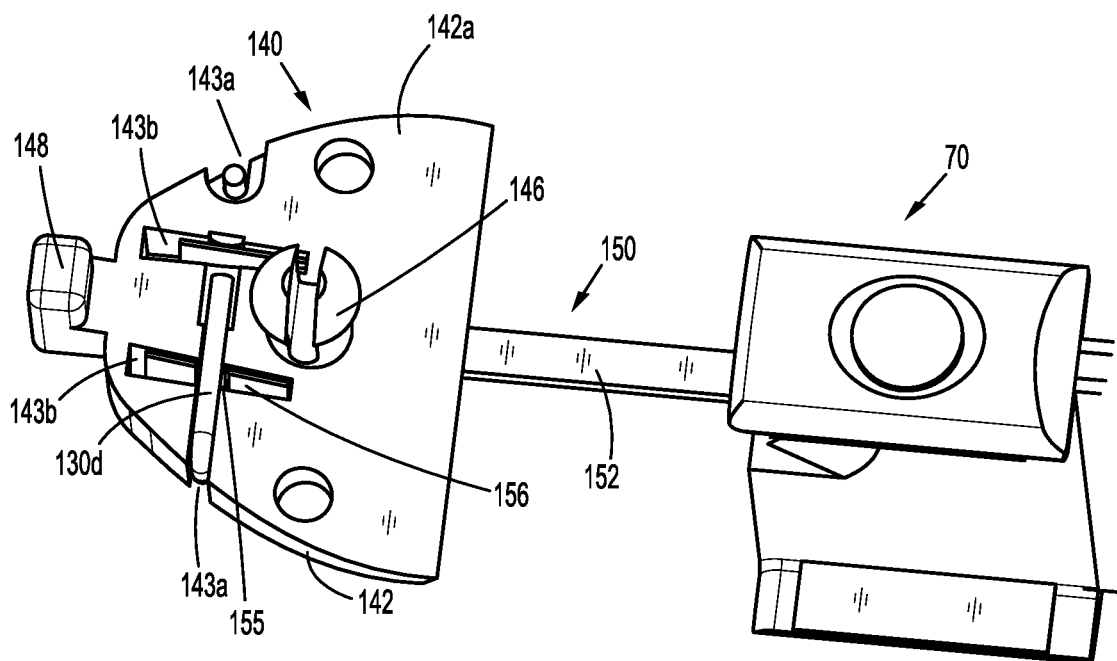
FIG. 4D is a top, perspective view of the anvil adapter, the anvil knife, and the retention member of the reload assembly of FIGS. 4A and 4B, shown coupled to an I-beam of a staple cartridge of the reload assembly.

As shown in FIGS. 4C and 4D, in conjunction with FIGS. 4A and 4B, the anvil knife 150 is coupled to the anvil adapter 140 and configured to cut the fourth retention member 130d upon actuation of the surgical stapling apparatus 1. The anvil knife 150 includes an elongated rod 152 having a proximal end 152a operatively engageable with the I-beam 70 of the staple cartridge 54 (FIG. 2), and a curved plate 154 extending distally from the elongated rod 152. The curved plate 154 has a plate body 154a and a pair of wings 154b extending upwardly from the plate body 154a, with at least one wing 154b having a recess 155 defined therein that includes an anvil knife blade 156 defined in an inner edge thereof.

The elongated rod 152 and the plate body 154a of the anvil knife 150 are positionable within a recess 145 defined in the tissue facing surface 142b of the anvil adapter 140 such that the pair of wings 154b of the anvil knife 150 project into the pair of elongated openings 143b of the anvil adapter 140. The anvil knife 150 is longitudinal movable relative to the anvil adapter 140 between proximal and distal positions within the confines of the recess 145 and the elongated openings 143b of the anvil adapter 140.

The fourth retention member 130d is threaded through the pair of recesses 143a of the anvil adapter 140 such that a portion of the fourth retention member 130d crosses the tissue facing surface 142b of the anvil adapter 140 and the plate body 154a of the anvil knife 150 (see e.g., FIG. 4B), and a portion of the fourth retention member 130d crosses through the recess 155 of the anvil knife 150 (see e.g., FIG. 4D).

The anvil adapter 140 further includes a button 146 extending outwardly from the anvil facing surface 142b of the body portion 142. The button 146 is configured to releasably engage the opening 45 (FIG. 2) of the anvil assembly 40. The button 146 includes a shank 146a and an enlarged head 146b extending from the shank 146a. A channel 147 is defined in the button 146 such that portions of the button 146 on opposed sides of the channel 147 may flex relative to each other. The anvil adapter 140 further includes a protrusion 148 disposed at a distal end thereof that is configured to releasably engage the notch 47 (FIG. 2) of the anvil assembly 40 and aid in maintaining alignment of the anvil adapter 140 with the anvil assembly 40.

With reference again to FIG. 3A, the shipping wedge 160 includes a generally elongate rectangular base 162 positionable between the surgical buttresses 110, 120, and detachably securable between the first and second jaw members 34a, 34b (FIG. 1) of the tool assembly 34. Components of the reload assembly 100 (e.g., surgical buttresses 110, 120, anvil adapter 140, etc.) may be releasably secured to the shipping wedge 160 to aid in loading/reloading the tool assembly 34. The shipping wedge 160 includes a proximal end 160a (FIG. 7) configured and dimensioned to prevent movement of the knife blade 68 (FIG. 2) while the shipping wedge 160 is installed on the tool assembly 34 (e.g., during shipment and/or prior to use), and a distal end 160b that is complementary in shape with the enlarged head 146b of the button 146 of the anvil adapter 140 to facilitate the release and removal of the anvil adapter 140 from the anvil assembly 40.

Figure 5C:
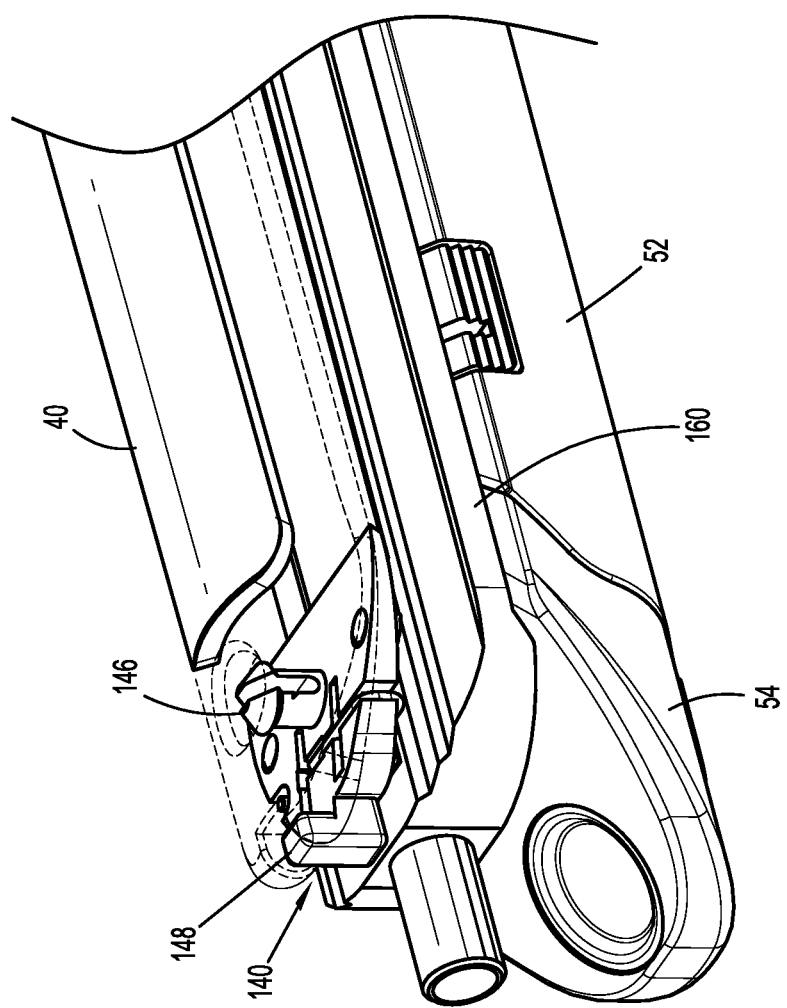
FIG. 5C is an enlarged view of a distal portion of the reload assembly of FIG. 5B, with an anvil plate of an anvil assembly of the first jaw member shown in phantom.

In a method of loading the reload assembly 100 onto the loading unit 30, as shown, for example, in FIG. 5A, with the loading unit 30 in the open position, the staple cartridge 54 is positioned within the carrier 52 of the second jaw member 34b of the tool assembly 34. As shown in FIG. 5B, the loading unit 30 is moved to the closed position such that the first and second jaw members 34a, 34b are approximated with respect to each other. As specifically shown in FIG. 5C, in conjunction with FIG. 5B, the button 146 and the latch 158 of the anvil adapter 140 engage the anvil assembly 40 such that when the tool assembly 34 is re-opened, the anvil buttress 120 is retained against the anvil assembly 40. The loading unit 30 is thus loaded and ready for use, upon removal of the shipping wedge 160 therefrom.

In operation, with the reload assembly 100 loaded onto the loading unit 30, as described above, and the shipping wedge 160 removed therefrom, the surgical stapling apparatus 1 is used in accordance with methods known by those skilled in the art. Once the anvil and staple cartridge assemblies 40, 50 are clamped onto tissue, the surgical stapling apparatus 1 is fired. In firing the surgical stapling apparatus 1, the drive beam 72 is advanced distally through the tool assembly 34 urging the staple pushers 62 upwardly which, in turn, drive the staples 60 out of the staple pockets 55 of the staple cartridge 54 and through the surgical buttresses 110, 120 as well as the captured tissue, thereby stapling the surgical buttresses 110, 120 to the tissue. The knife blade 68 substantially simultaneously cuts and divides the tissue and the surgical buttresses 110, 120 disposed between the rows of now formed staples 60.

Figure 6A:
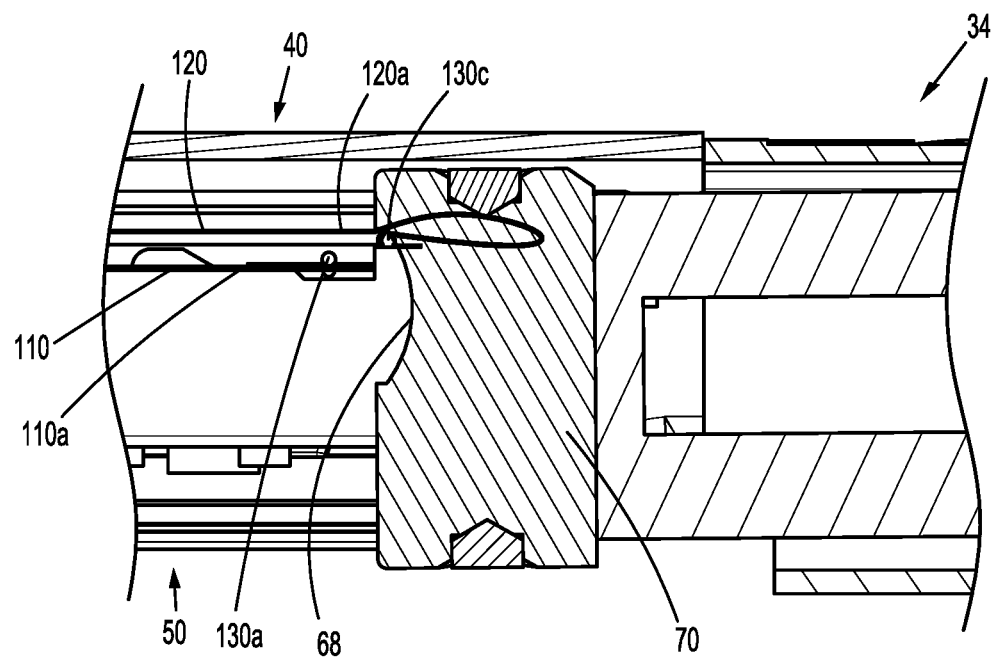
FIG. 6A is a side, cross-sectional view of a proximal portion of a tool assembly of the surgical stapling apparatus of FIG. 1 that is loaded with the reload assembly of FIG. 3A, during actuation of the surgical stapling apparatus.

During firing, as shown in FIG. 6A, the knife blade 68 of the I-beam 70 travels distally through the tool assembly 34. As the first and third retention members 130a, 130c extend across the respective proximal portions 110a, 120a of the cartridge and anvil buttresses 110, 120 above the respective central longitudinal slots 57, 41 (FIG. 2) of the staple cartridge and anvil assemblies 50, 40, the knife blade 68 also cuts through the third retention member 130c and then the first retention member 130a thereby freeing the proximal portions 120a, 110a of the anvil and cartridge buttresses 120, 110 from the anvil and staple cartridge assemblies 40, 50.

Figure 6B:
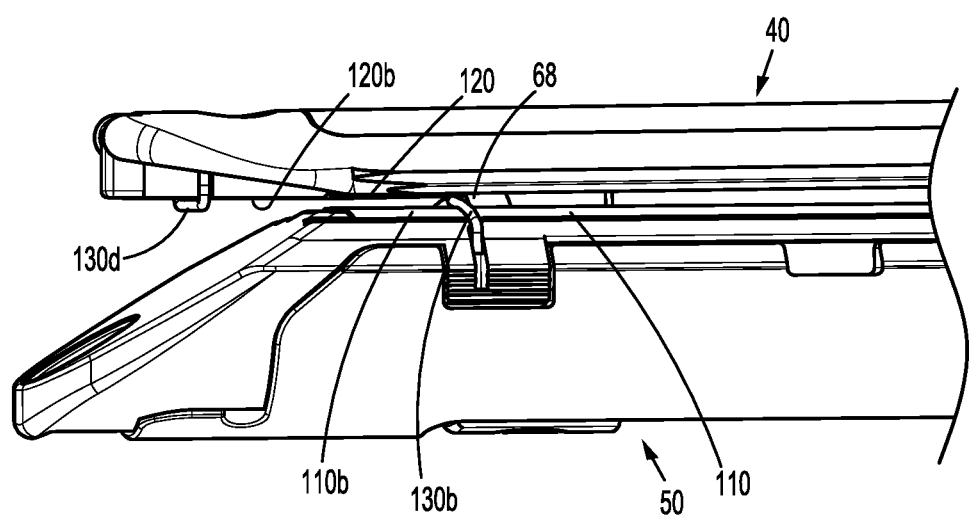
FIG. 6B is a side, plan view of a distal portion of the tool assembly of FIG. 6A during actuation of the surgical stapling apparatus.
Figure 6C:
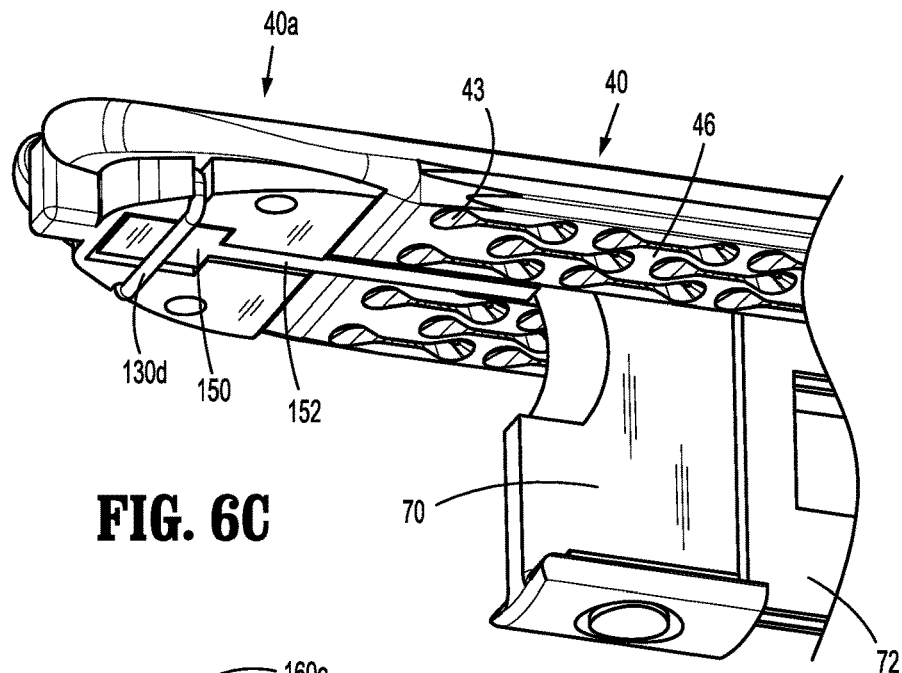
FIG. 6C is a bottom perspective view of a first jaw member of the tool assembly of FIG. 6B during actuation of the surgical stapling apparatus, with parts removed.

As the knife blade 68 continues to travel distally, as shown in FIG. 6B, to divide the cartridge buttress 120 longitudinally along a length thereof. As the knife blade 68 approaches the distal ends of the anvil and the cartridge assemblies 40, 50, the knife blade 68 cuts the second retention member 130b, which extends across the distal portion 110b of the cartridge buttress 110 above the central longitudinal slot 57 (FIG. 2) of the staple cartridge assembly 50, thereby releasing the distal portion 110b of the cartridge buttress 110 from the staple cartridge assembly 50. As shown in FIG. 6C, in conjunction with FIG. 6B, continued distal movement of the I-beam 70 causes the I-beam 70 to contact the elongated rod 152 of the anvil knife 150 and to move the anvil knife 150 distally which, in turn, cuts the fourth retention member 130d thereby releasing the distal portion 120b of the anvil buttress 120 from the anvil assembly 40.

When firing is complete and the anvil and staple cartridge assemblies 40, 50 are unclamped, the anvil and cartridge buttresses 120, 110, which are now stapled to the tissue, pull away from the anvil and staple cartridge assemblies 40, 50, and the tool assembly 34 is removed from the surgical site. The used reload assembly 100 may then be removed from the tool assembly 34 by removing the staple cartridge 54 from the staple cartridge assembly 50 and the anvil adapter 140 from the anvil assembly 40.

Figure 7:
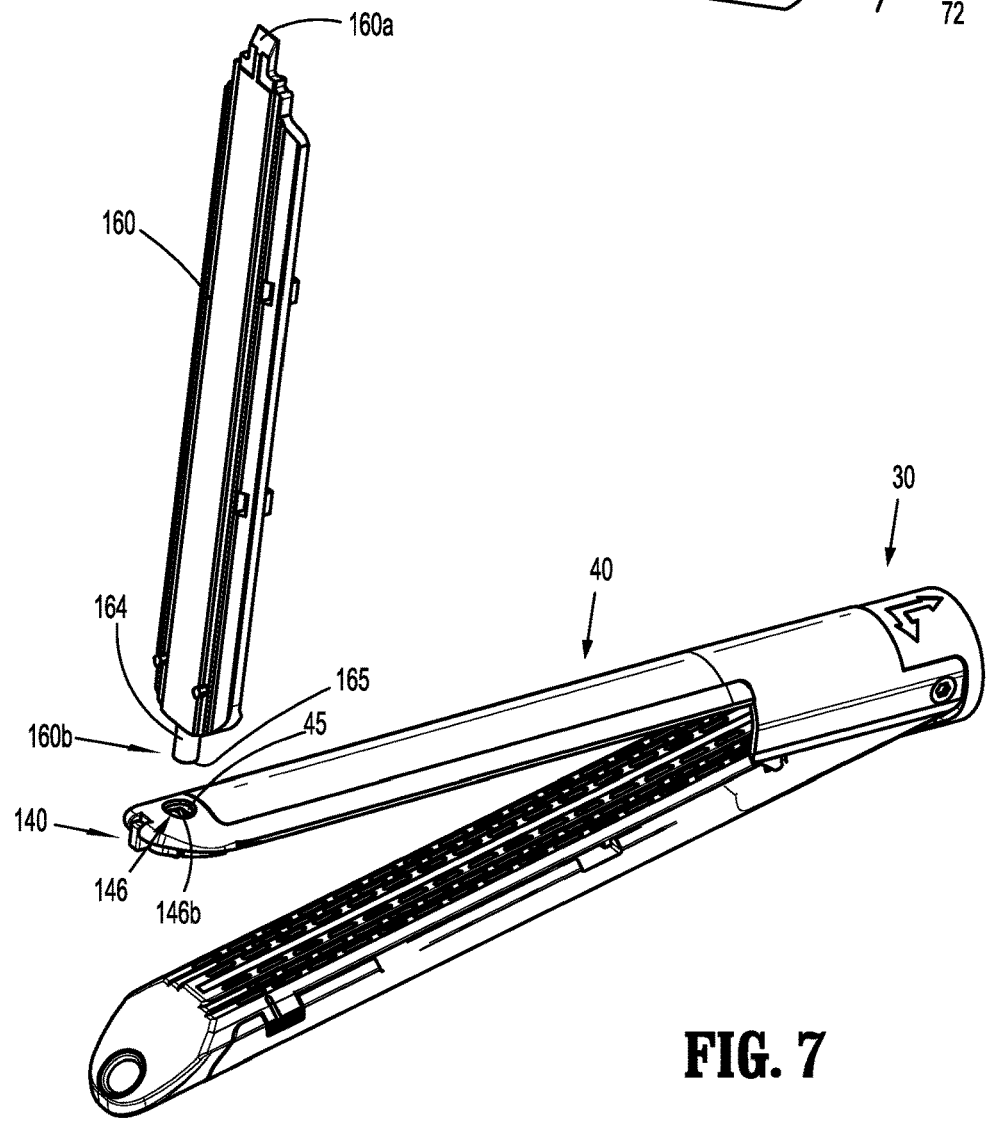
FIG. 7 is a side, perspective view of a tool assembly during removal of an anvil adapter therefrom.

As shown in FIG. 7, the anvil adapter 140 may be removed from the anvil assembly 40 by inserting the distal end 160b of the shipping wedge 160 into the opening 45 of the anvil assembly 40 such that the distal end 160b of the shipping wedge 160 engages the enlarged head 146b of the button 146 of the anvil adapter 140. The distal end 160b of the shipping wedge 160 includes a cylindrical body 164 defining an opening 165 therein that is configured to engage and squeeze the enlarged head 146b of the button 146 of the anvil adapter 140 and to push the button 146 out of the opening 45, thereby releasing the anvil adapter 140 from the anvil assembly 40. A new reload assembly 100 may be loaded onto the loading unit 30, as described above.

Figure 8A:
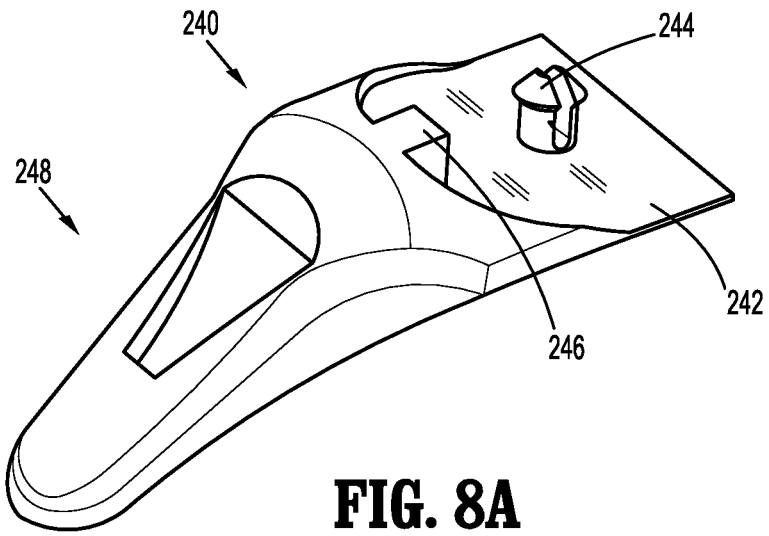
FIG. 8A is a front, perspective view of an anvil adapter in accordance with another embodiment of the present disclosure.
Figure 8B:
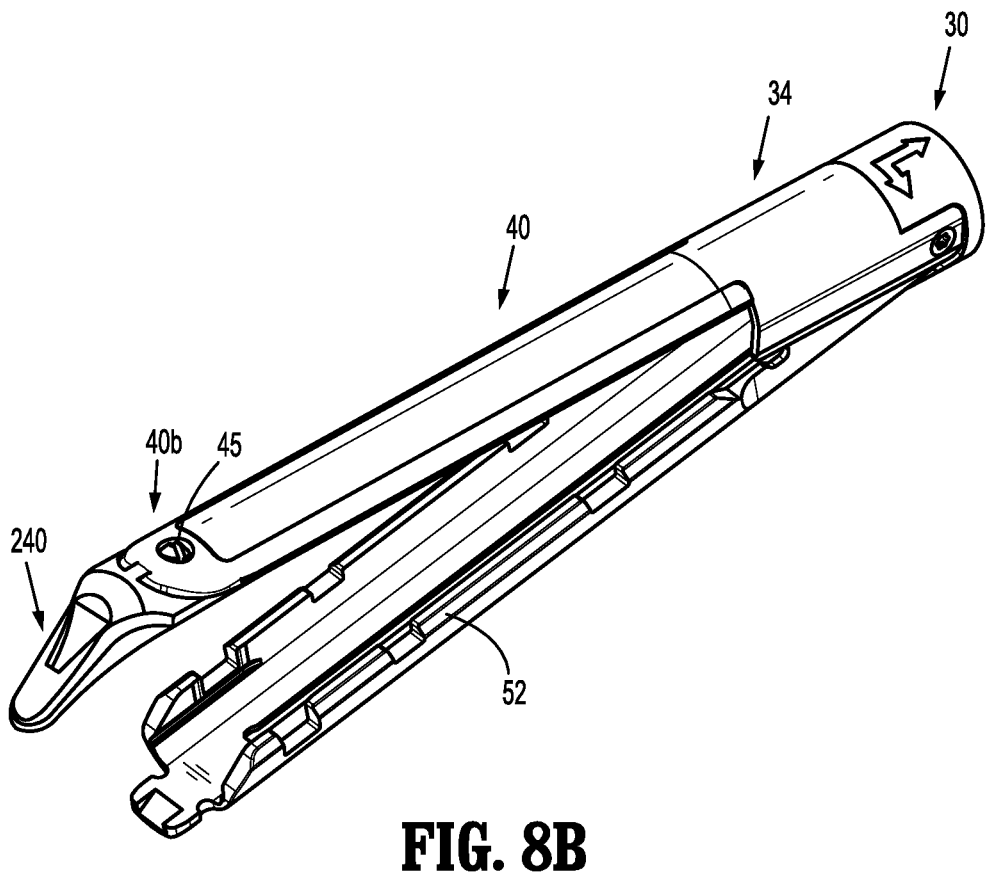
FIG. 8B is a front, perspective view of the anvil adapter of FIG. 8A loaded onto a tool assembly of a loading unit.

An anvil adapter 240 in accordance with another embodiment of the present disclosure is shown in FIGS. 8A and 8B. The anvil adapter 240 includes a body portion 242 configured and dimensioned to engage a distal portion 40b of the anvil assembly 40. The body portion 242 of the anvil adapter 240 includes a button 244, as described above with regard to button 146 of anvil adapter 140, for releasably engaging the opening 45 of the anvil assembly 40, and a protrusion 246 for maintaining alignment of the anvil adapter 240 with the anvil assembly 40.

The anvil adapter 240 further includes a tip portion 248 configured and dimensioned to provide the loading unit 30 with a curved tip to enhance visualization and/or maneuverability of the tool assembly 34 around target tissue and/or vessels. The tip portion 248 of the anvil adapter 240 may aid in tissue manipulation, allowing for blunt tissue dissection and/or mobilization. Other configurations of the tip portion 248 are envisioned depending upon, for example, the desired characteristics of the tool assembly 34 as should be understood by those skilled in the art. Accordingly, it should be understood that a clinician can customize a loading unit to have a desired configuration for a particular surgical procedure and/or patient. It should be further understood that the reload assembly 100 may be used with anvil adapters having a variety of configurations. For example, the anvil adapter 140 of the reload assembly 100 may be modified to include the tip portion 248 of the anvil adapter 240. Accordingly, a variety of combinations of the components of the reloads and/or anvil adapters are envisioned.

It should be further understood that while the reload assembly 100 is shown including both cartridge and anvil buttresses 110, 120, the reload assembly 100 may include only the cartridge buttress or the anvil buttress 120 depending on, for example, the surgical application and/or the desired placement of the buttress material relative to tissue as should be understood by those skilled in the art.

The surgical buttress reloads and tip attachment assemblies described herein may also be configured for use with other surgical apparatus, such as electromechanical surgical devices as described, for example, in U.S. Patent Appl. Pub. Nos. 2015/0157320 and 2015/0157321, the entire contents of each of which are incorporated herein by reference. Furthermore, the surgical stapling instrument could be configured for use in a surgical robotic system.

In any of the embodiments disclosed herein, a removable and replaceable staple cartridge can be provided for use with a surgical reload, or a surgical stapling instrument having a jaw attached to an elongate portion, without a loading unit that has an portion removably attachable to the elongate portion of a handle. In any of the embodiments disclosed herein, the surgical buttress can be made from a melt blown bioabsorbable material, such as polyglycolic acid, polylactic acid, glycolide trimethylene carbonate, and polycaprolactone. The surgical buttress can include, be coated with, or otherwise deliver a bioactive material, such as a medicament, hemostat, growth factors, chemotherapy agent, or other such materials.

While the surgical stapling apparatus of the present disclosure are shown firing staples, it should be understood that the surgical stapling apparatus may be adapted to fire other fasteners, such as clips, two-part fasteners, among other suitable fasteners within the purview of those skilled in the art.

Persons skilled in the art will understand that the systems, devices, and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A surgical stapling apparatus comprising:
    a loading unit including:
        a staple cartridge assembly; and
        an anvil assembly including a tissue facing surface; and
    a reload assembly, the reload assembly including:
        a staple cartridge;
        an anvil adapter including a body having an anvil facing surface and a tissue facing surface; and
        an anvil buttress,
        the reload assembly having an assembled state in which a proximal portion of the anvil buttress is releasably secured to the staple cartridge and a distal portion of the anvil buttress is releasably secured to the anvil adapter, the reload assembly releasably coupled to the loading unit in the assembled state with the staple cartridge releasably disposed within the staple cartridge assembly and the anvil adapter releasably coupled to the anvil assembly, the anvil facing surface of the anvil adapter positioned against the tissue facing surface of the anvil assembly.

2. The surgical stapling apparatus according to claim 1, wherein the anvil assembly includes an opening defined therethrough and the anvil adapter includes a button releasably engaged with the opening.

3. The surgical stapling apparatus according to claim 2, wherein the reload assembly includes a shipping wedge having an elongate base and a distal end extending from the elongate base, the distal end being complementary in shape with the button of the anvil adapter to facilitate release of the button from the opening of the anvil assembly.

4. The surgical stapling apparatus according to claim 1, wherein the anvil adapter includes a protrusion extending from a distal end thereof and the anvil assembly includes a notch defined in a distal end thereof, the protrusion releasably engaged with the notch.

5. The surgical stapling apparatus according to claim 1, wherein the anvil assembly includes an anvil plate having the tissue facing surface.

6. The surgical stapling apparatus according to claim 5, wherein the anvil assembly includes a cover plate secured over the anvil plate.

7. The surgical stapling apparatus according to claim 1, wherein the reload assembly includes a retention member releasably securing the distal portion of the anvil buttress to the anvil adapter.

8. The surgical stapling apparatus according to claim 7, wherein the retention member is an elongated strand of material.

9. The surgical stapling apparatus according to claim 7, wherein the reload assembly includes an anvil knife configured to cut the retention member and release the distal portion of the anvil buttress from the anvil adapter.

10. The surgical stapling apparatus according to claim 9, wherein the anvil knife includes an anvil knife blade disposed within an elongate opening defined in the anvil adapter, the anvil knife blade longitudinally movable within the elongate opening to cut a portion of the retention member extending across the elongate opening.

11. The surgical stapling apparatus according to claim 1, wherein the proximal portion of the anvil buttress is secured to the staple cartridge by a retention member.

12. The surgical stapling apparatus according to claim 1, wherein the proximal portion of the anvil buttress is secured to a trailing portion of the staple cartridge, the trailing portion facing the anvil assembly.

13. The surgical stapling apparatus according to claim 1, wherein the proximal portion of the anvil buttress is a loop of buttress material.

14. The surgical stapling apparatus according to claim 1, wherein the reload assembly further includes a cartridge buttress releasably secured to the staple cartridge.

15. The surgical stapling apparatus according to claim 14, wherein proximal and distal portions of the cartridge buttress are releasably secured to a tissue facing surface of the staple cartridge.

16. The surgical stapling apparatus according to claim 14, wherein the reload assembly includes a shipping wedge releasably positioned between the cartridge and anvil buttresses.

17. The surgical stapling apparatus according to claim 1, wherein the anvil adapter includes a tip portion having a curved dissecting tip.

18. A method of loading a reload assembly onto a loading unit, the method comprising: releasably coupling a reload assembly to a loading unit in an assembled state,
    the loading unit including:
        a staple cartridge assembly; and
        an anvil assembly having a tissue facing surface; and
    the reload assembly including:
        a staple cartridge;
        an anvil adapter including a body having an anvil facing surface and a tissue facing surface; and
        an anvil buttress,
    wherein the reload assembly is in the assembled state, a proximal portion of the anvil buttress is releasably secured to the staple cartridge and a distal portion of the anvil buttress is releasably secured to the anvil adapter, the reload assembly releasably coupled to the loading unit in the assembled state by:
        releasably positioning the staple cartridge within the staple cartridge assembly; and
        releasably coupling the anvil adapter to the anvil assembly with the anvil facing surface of the anvil adapter positioned against the tissue facing surface of the anvil assembly.

19. The method according to claim 18, further comprising moving the loading unit from an open position to a closed position after releasably positioning the staple cartridge within the staple cartridge assembly to releasably couple the anvil adapter to the anvil assembly.

20. The method according to claim 18, further comprising removing a shipping wedge positioned between the staple cartridge and the anvil buttress from the reload assembly.

* * * * *